US012296231B2

(12) United States Patent
Hwang

(10) Patent No.: US 12,296,231 B2
(45) Date of Patent: May 13, 2025

(54) APPARATUS FOR SELECTING HIGH-QUALITY GOLF BALL

(71) Applicant: EMTELLI INC., Suwon-si (KR)

(72) Inventor: Keum Cheol Hwang, Seoul (KR)

(73) Assignee: EMTELLI INC., Suwon-si (KR)

( * ) Notice: Subject to any disclaimer, the term of this patent is extended or adjusted under 35 U.S.C. 154(b) by 0 days.

(21) Appl. No.: 17/907,609

(22) PCT Filed: Jun. 21, 2022

(86) PCT No.: PCT/KR2022/008762
§ 371 (c)(1),
(2) Date: Sep. 28, 2022

(87) PCT Pub. No.: WO2022/270864
PCT Pub. Date: Dec. 29, 2022

(65) Prior Publication Data
US 2024/0207693 A1 Jun. 27, 2024

(30) Foreign Application Priority Data

Jun. 24, 2021 (KR) .......... 10-2021-0082339
Sep. 29, 2021 (KR) .......... 10-2021-0128704

(51) Int. Cl.
*A63B 47/00* (2006.01)
*G01N 22/02* (2006.01)
*A63B 102/32* (2015.01)

(52) U.S. Cl.
CPC ........... *A63B 47/008* (2013.01); *G01N 22/02* (2013.01); *A63B 2102/32* (2015.10)

(58) Field of Classification Search
CPC .............................. A63B 47/00; A63B 47/008
See application file for complete search history.

(56) References Cited

U.S. PATENT DOCUMENTS

| 4,289,032 A | * | 9/1981 | Tominaga | ............... | G01N 29/11 |
| | | | | | 473/409 |
| 6,085,578 A | * | 7/2000 | Tanaka | ................... | G01M 1/16 |
| | | | | | 73/65.02 |
| 11,058,924 B1 | | 7/2021 | Caterina et al. | | |
| 11,543,241 B1 | * | 1/2023 | Furze | ................... | G01B 15/045 |

(Continued)

FOREIGN PATENT DOCUMENTS

| DE | 3926684 A1 | * | 2/1991 | | |
| FR | 2708472 A1 | * | 2/1995 | ......... | A63B 24/0021 |

(Continued)

OTHER PUBLICATIONS

Office Action dated Jul. 17, 2023 in Korean Application No. 10-2021-0128704.

(Continued)

*Primary Examiner* — Alvin A Hunter
(74) *Attorney, Agent, or Firm* — SALIWANCHIK, LLOYD & EISENSCHENK

(57) ABSTRACT

Disclosed is an apparatus for selecting a high-quality golf ball, the apparatus including a measurer configured to transmit a signal toward a golf ball and receive a signal reflected from the golf ball or a signal transmitted through the golf ball; and an analyzer configured to select a golf ball by analyzing the received signal.

14 Claims, 17 Drawing Sheets

(56) References Cited

U.S. PATENT DOCUMENTS

| | | | | |
|---|---|---|---|---|
| 11,668,560 | B1 * | 6/2023 | Furze | A63B 37/0077 |
| | | | | 378/62 |
| 11,752,396 | B1 * | 9/2023 | Caterina | G01N 23/083 |
| | | | | 378/62 |
| 11,874,106 | B1 * | 1/2024 | Furze | G01B 15/045 |
| 2005/0164808 | A1 * | 7/2005 | Sasaki | A63B 43/00 |
| | | | | 473/351 |
| 2015/0084645 | A1 * | 3/2015 | Kayano | H01Q 1/364 |
| | | | | 324/639 |
| 2015/0087443 | A1 * | 3/2015 | Kitazaki | A63B 37/0039 |
| | | | | 473/373 |
| 2022/0184463 | A1 * | 6/2022 | Ganson | A63B 24/0021 |

FOREIGN PATENT DOCUMENTS

| | | | | | |
|---|---|---|---|---|---|
| JP | 55063758 | A | * | 5/1980 | |
| JP | 4-364402 | A | | 12/1992 | |
| JP | 06126015 | A | * | 5/1994 | |
| JP | 6-237090 | A | | 8/1994 | |
| JP | 8-271446 | A | | 10/1996 | |
| JP | 9-214131 | A | | 8/1997 | |
| JP | 2004-230325 | A | | 8/2004 | |
| JP | 2004-523768 | A | | 8/2004 | |
| JP | 2005205091 | A | * | 8/2005 | ......... A63B 37/0003 |
| JP | 2011-215150 | A | | 10/2011 | |
| JP | 2013-195219 | A | | 9/2013 | |
| JP | 2015-87378 | A | | 5/2015 | |
| JP | 2018-72252 | A | | 5/2018 | |
| KR | 97-58431 | A | | 7/1997 | |
| KR | 10-2013-0112115 | A | | 10/2013 | |
| KR | 10-2017-0136906 | A | | 12/2017 | |
| KR | 10-2012601 | B1 | | 8/2019 | |
| WO | WO-2022270864 | A1 | * | 12/2022 | ......... A63B 37/0003 |

OTHER PUBLICATIONS

Office Action dated Apr. 20, 2023 in Korean Application No. 10-2021-0082339.
International Search Report dated Sep. 29, 2022 in International Application No. PCT/KR2022/008762.
Office Action dated Jan. 9, 2024 in Japanese Application No. 2023-506290.

* cited by examiner

APPARATUS FOR SELECTING HIGH-QUALITY GOLF BALL

CROSS-REFERENCE TO RELATED APPLICATIONS

This application is the U.S. national stage application of International Patent Application No. PCT/KR2022/008762, filed Jun. 21, 2022, which claims the benefit under 35 U.S.C. § 119 of Korean Application Nos. 10-2021-0082339, filed Jun. 24, 2021; and 10-2021-0128704, filed Sep. 29, 2021; the disclosures of each of which are incorporated herein by reference in their entirety.

TECHNICAL FIELD

The disclosure relates to an apparatus for selecting a high-quality golf ball, and more particularly to an apparatus for selecting a high-quality golf ball, in which an electromagnetic signal is used to select the high-quality golf ball that is close to symmetry and internally and externally uniform including a core, an inner shell, and an outer shell.

BACKGROUND ART

A golf ball has a structure including a core and a cover, and is classified into two-piece, three-piece, four-piece, etc. golf balls according to layered structures. With recent development of manufacturing technology, the three-piece golf ball including a core, an inner shell, and an outer shell or the four-piece golf ball including double cores, an inner shell, and an outer shell has been generally available to not only tour pro golfers but also amateur golfers.

About 40 million dozen golf balls are produced a year. During the production, problems of an eccentric core (2.78%), an imbalanced internal medium (11.11%), a damaged outer shell (2.78%), etc. arise frequently. Such problems act as a hindrance to consistent shots.

Defects due to the damaged outer shell are detectable by a human in person through a visual or tactile sense, or by an image analysis after taking its image. On the other hand, defects due to the eccentric core or imbalanced internal medium are detectable by a method of floating the golf ball in a liquid mixed with salt water and surfactant. However, such a conventional method is not suitable for a production process because it takes long time to detect the defects. Accordingly, there are currently no suitable means for detecting the imbalanced internal medium of the golf ball.

DISCLOSURE

Technical Problem

Accordingly, the disclosure is conceived to solve such problems as described above, and an aspect of the disclosure is to provide an apparatus for selecting a high-quality golf ball, which transmits an electromagnetic signal toward a golf ball and receives and analyzes an electromagnetic signal transmitted through or reflected from the golf ball, thereby selecting the high-quality golf ball that is internally and externally uniform and close to symmetry.

The problems to be solved by the disclosure are not limited to those mentioned above, and other unmentioned problems will become apparent to a person skilled in the art by the following descriptions.

Technical Solution

The aspect of the disclosure may be achieved byan apparatus for selecting a high-quality golf ball, including: a measurer configured to transmit a signal toward a golf ball and receive a signal reflected from the golf ball or a signal transmitted through the golf ball; and an analyzer configured to select a golf ball by analyzing the received signal.

Here, the measurer may include a rotary supporter configured to rotatably support the golf ball; an electromagnetic wave transmitting antenna disposed at a first side of the golf ball and configured to transmit electromagnetic waves toward the golf ball; and an electromagnetic wave receiving antenna disposed at a second side of the golf ball and configured to receive electromagnetic waves transmitted from the electromagnetic wave transmitting antenna.

Here, the measurer may include: a rotary supporter configured to rotatably support the golf ball; and an electromagnetic wave transceiving antenna disposed at a first side of the golf ball and configured to transmit electromagnetic waves toward the golf ball and receive reflected electromagnetic waves from the golf ball.

Here, the rotary supporter may include a golf ball supporter to support the golf ball to be vertically spaced apart from the ground; and a rotation unit to rotate the golf ball supporter with respect to a vertical axis, and the apparatus may further include a first antenna supporter and a second antenna supporter which are spaced apart from the golf ball supporter and respectively support the electromagnetic wave transmitting antenna and the electromagnetic wave receiving antenna to be located on the same horizontal plane as the golf ball supported by the golf ball supporter.

Here, the rotary supporter may include a golf ball supporter to support the golf ball to be vertically spaced apart from the ground; and a rotation unit to rotate the golf ball supporter with respect to a vertical axis, and the apparatus may further include an antenna supporter which is spaced apart from the golf ball supporter and supports the electromagnetic wave transceiving antenna to be located on the same horizontal plane as the golf ball supported by the golf ball supporter.

Here, The apparatus may further include a base configured to support the golf ball supporter and the antenna supporter on one side thereof, wherein the base includes an absorber attached or applied to the one side of the base and absorbing diffusely reflected electromagnetic waves.

Here, the antenna supporter may be slidably provided with respect to the golf ball supporter and adjustable in distance from the golf ball supporter.

Here, the rotary supporter may include a first rotation supporting plate configured to support a first point on a lateral side of the golf ball and rotated by a motor; and a second rotation supporting plate configured to support a second point on a lateral side of the golf ball and rotated by a motor.

Here, the first point and the second point may be two points orthogonal to each other with respect to the center of the golf ball when viewed from top to bottom.

Here, the rotary supporter may further include a roll bar that is freely rotatable at opposite sides thereof, and supports a third point of the golf ball.

Here, the signal may include a radio frequency (RF) electromagnetic signal.

Here, the signal may include electromagnetic waves, and the apparatus may further include a detector that generates and transceives the electromagnetic waves, and outputs and detects the magnitude and phase of the received electromagnetic waves.

Here, the detector may include a transmitting circuit and a receiving circuit, include a network analyzer, or include a signal generator and a spectrum analyzer.

Here, the analyzer may be configured to select a high-quality golf ball, which is internally and externally uniform and close to symmetry, based on the uniformity of a signal received with respect to a plurality of measurement sides while rotating the golf ball.

Here, the analyzer may be configured to select a high-quality golf ball, which is internally and externally uniform and close to symmetry, based on the uniformity of the magnitude and phase of the signal received with respect to the plurality of measurement sides.

Here, the analyzer may be configured to select a high-quality golf ball, which is internally and externally uniform and close to symmetry, based on the magnitude and phase of the signal received with respect to the plurality of measurement sides based on deep learning.

Advantageous Effects

As described above, an apparatus for selecting a high-quality golf ball according to the disclosure has advantage that is capable to select the high-quality golf ball that is close to symmetry and internally and externally uniform easily and quickly by using an electromagnetic signal.

DESCRIPTION OF DRAWINGS

The above and/or other aspects of the disclosure will become apparent and more readily appreciated from the following description of the exemplary embodiments, taken in conjunction with the accompanying drawings, in which.

MODE FOR CARRYING OUT DISCLOSURE

Below, embodiments of an apparatus for selecting a high-quality golf ball according to the disclosure will be described with reference to the accompanying drawings.

Figure 1:
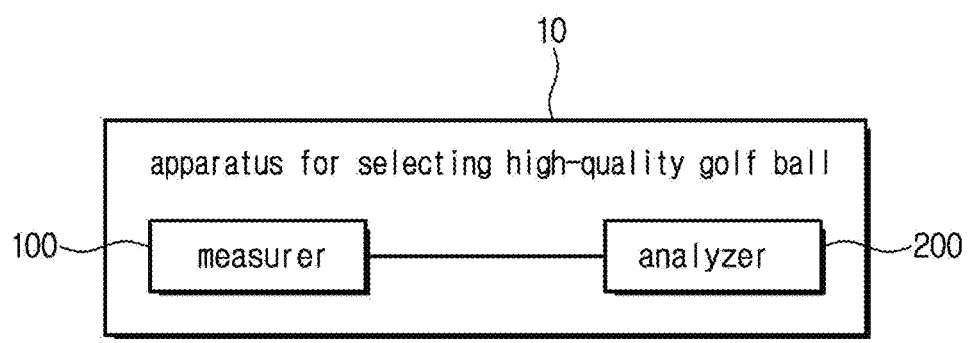
FIG. 1 is a block diagram schematically showing the configuration of an apparatus for selecting a high-quality golf ball according to an embodiment of the disclosure.

FIG. 1 is a block diagram schematically showing the configuration of an apparatus for selecting a high-quality golf ball according to an embodiment of the disclosure.

The apparatus for selecting a high-quality golf ball according to an embodiment of the disclosure may include a measurer 100 and an analyzer 200.

The measurer 100 may transmit a signal toward a measurement target golf ball, and receive a signal reflected from or transmitted through the golf ball. In this case, the signal may be transmitted and received with respect to a plurality of measurement sides of the golf ball. Here, the measurement side may be perpendicular to the direction of signal to be transmitted. The signal may be electromagnetic waves, and may for example include, but not limited to, a radio frequency (RF) electromagnetic signal.

To check the responses of the reflected or transmitted electromagnetic waves to the plurality of measurement sides of the measurement target golf ball, the measurer 100 receives first electromagnetic waves reflected or transmitted after rotating the measurement target golf ball at an arbitrary angle, and receives second electromagnetic waves reflected or transmitted after rotating the measurement target golf ball at an arbitrary angle. In this way, the measurement may be repeated for the plurality of measurement sides by rotating the golf ball and transmitting and receiving the electromagnetic waves.

In this case, the measurer 100 may include a rotary supporter rotatably supporting a measurement target golf ball, an electromagnetic wave transmitting antenna 110 disposed at a first side of the golf ball and configured to transmit electromagnetic waves toward the golf ball, and an electromagnetic wave receiving antenna 120 disposed at a second side of the golf ball and configured to receive the electromagnetic waves transmitted from the electromagnetic wave transmitting antenna 110. In other words, the electromagnetic signal transmitted from the electromagnetic wave transmitting antenna 110 at the first side of the golf ball is received in the electromagnetic wave receiving antenna 120 at the second side of the golf ball, thereby receiving the electronic signal transmitted through the golf ball.

Alternatively, the measurer 100 may include a rotary supporter rotatably supporting a measurement target golf ball, and an electromagnetic wave transceiving antenna 1120 disposed at a first side of the golf ball and configured to transmit electromagnetic waves toward the golf ball and receive the electromagnetic waves reflected from the golf ball. In other words, the electromagnetic signal transmitted from the electromagnetic wave transceiving antenna 1120 disposed at the first side of the golf ball is reflected from the golf ball and received in the electromagnetic wave transceiving antenna 1120.

Details of the measurer 100 will be described later.

The analyzer 200 analyzes signals received with respect to a plurality of measurement sides while rotating the golf ball, thereby selecting a high-quality golf ball. For example, if the core in the golf ball has a uniform spherical shape, and the core, inner shell, and outer shell of the golf ball have a symmetric structure, the signals received while rotating the golf ball may have high uniformity. In other words, the electromagnetic waves reflected from or transmitted through the plurality of measurement sides are highly similar in magnitude and phase. It is estimated that the greater the difference in magnitude and phase between the electromagnetic waves reflected from or transmitted through the measurement sides, the greater the non-uniformity inside the golf ball. Therefore, the analyzer 200 according to the disclosure selects a high-quality golf ball, which has a uniform internal medium and is close to symmetry, based on the uniformity of the signals received while the rotary supporter rotates the golf ball.

The analyzer 200 may be configured as software installed in a computer including a computing device and a storage device, or a smart device such as a smartphone.

According to an embodiment, the analyzer 200 may use a deep learning technique to estimate the eccentricity or imbalance of the medium inside the golf ball. The analyzer 200 may use the deep learning technique to grade the eccentricity or imbalance of the golf ball, or use a preset criterion to determine a defect.

Figure 2:
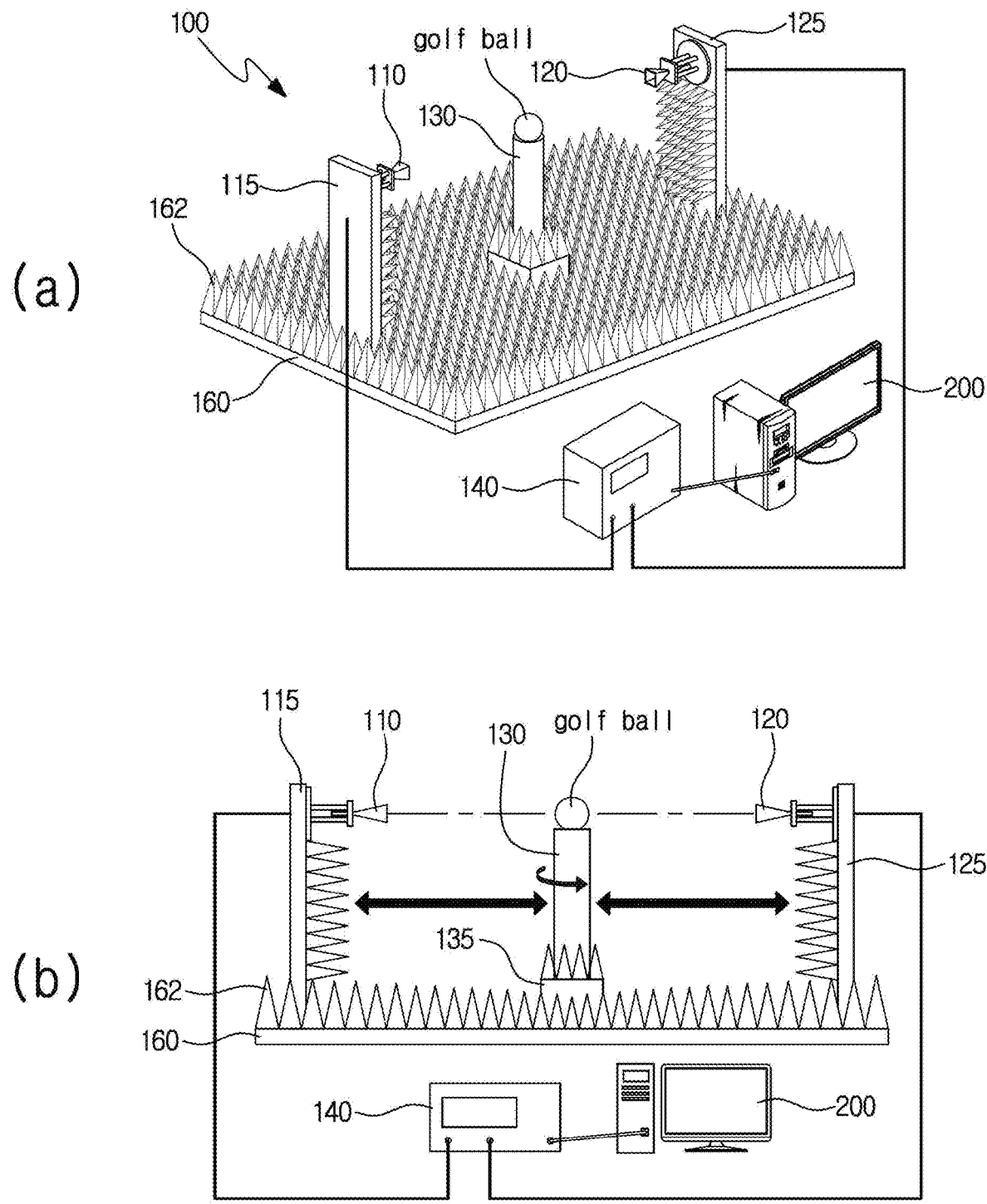
FIG. 2 shows perspective and lateral views of an apparatus for selecting a high-quality golf ball according to an embodiment of the disclosure.
Figure 3:
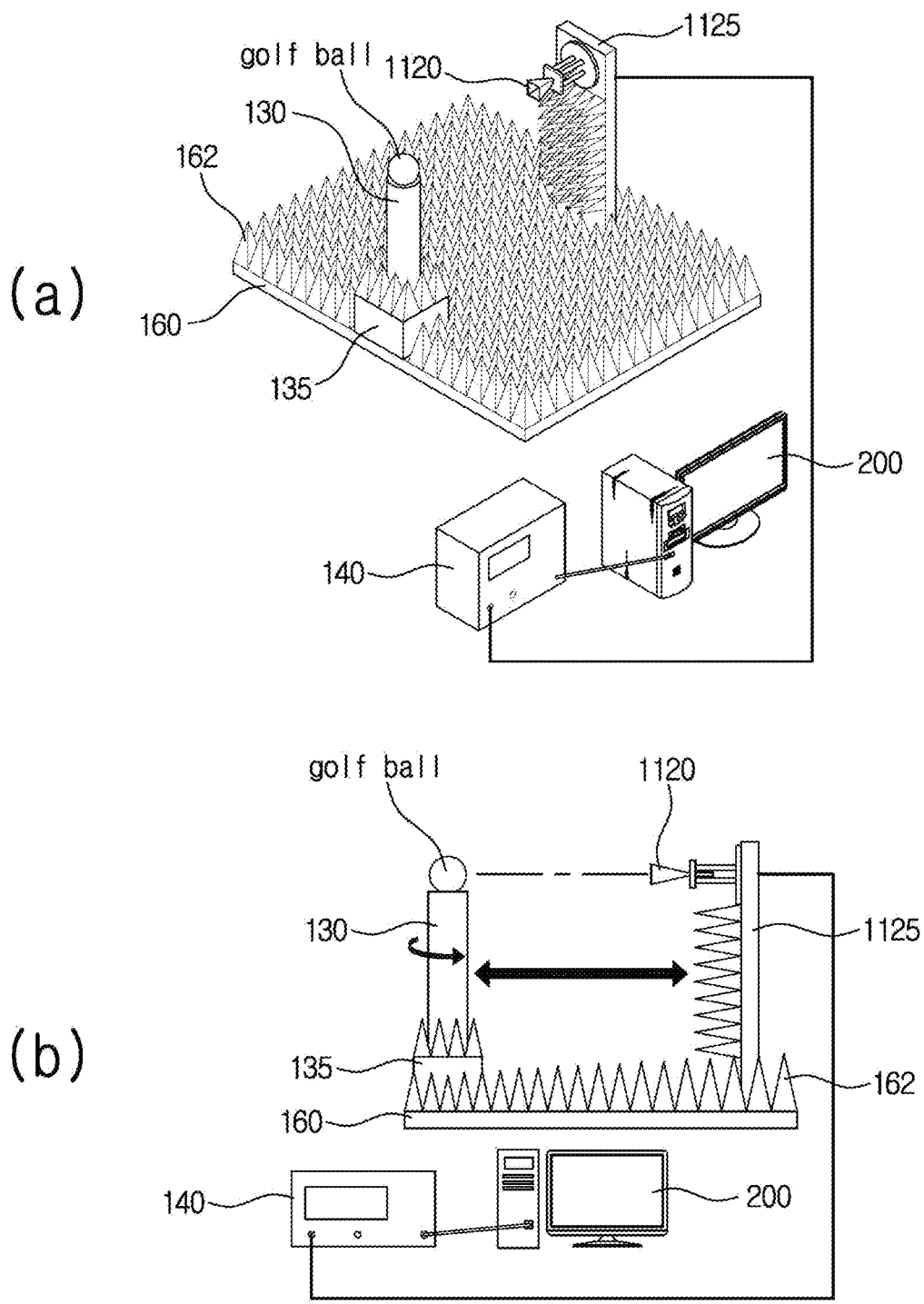
FIG. 3 shows an alternative example of FIG. 2.

FIG. 2 shows perspective and lateral views of an apparatus for selecting a high-quality golf ball according to an embodiment of the disclosure, and FIG. 3 shows an alternative example of FIG. 2.

Referring to FIG. 2, the measurer 100 in the apparatus for selecting a high-quality golf ball according to an embodiment may include a rotary supporter and two antennas 110 and 120.

The rotary supporter may include a golf ball supporter 130 and a rotation unit 135. The golf ball supporter 130 supports the measurement target golf ball to be vertically spaced apart from the ground. As shown therein, the golf ball supporter 130 may be shaped like a bar extended vertically upwards from the ground, and includes an upper end on which a golf ball is seated. The rotation unit 135 rotates the golf ball supporter 130 with respect to a vertical axis. As the golf ball supporter 130 is rotated by the rotation unit 135, the measurement side of the golf ball, to which the electromagnetic wave transmitting antenna 110 transmits the electromagnetic waves, is changed. In this case, the rotation unit 135 may rotate the golf ball by a predetermined angle. The rotation unit 135 may include a motor for rotating the golf ball supporter 130.

Further, the measurer 100 of FIG. 2 may additionally include antenna supporters 115 and 125. The antenna supporters 115 and 125 include a first antenna supporter 115 and a second antenna supporter 125 which are spaced apart from the golf ball supporter 130 and respectively support the electromagnetic wave transmitting antenna 110 and the electromagnetic wave receiving antenna 120 to be located on the same horizontal plane as the golf ball supported by the golf ball supporter 130.

Furthermore, the measurer 100 of FIG. 2 may further include a base 160 to support the golf ball supporter 130 and the antenna supporters 115 and 125 on one side thereof. In this case, the base 160 is formed with sliding holes (not shown) on one side thereof between the antenna supporters 115 and 125 and the golf ball supporter 130 so that the antenna supporters 115 and 125 can be slidably coupled to the sliding holes. Therefore, the antenna supporters 115 and 125 are adjustable in distance from the golf ball supporter 130.

The golf ball supporter 130 and the antenna supporters 115 and 125 are vertically extendable so that a target to be supported can be adjusted in vertical distance from the base 160.

An absorber 162 for absorbing electromagnetic waves may be attached or applied to one side of the base 160. The absorber 162 may contain, but is not necessarily limited to, ferrite. The absorber 162 may absorb the electromagnetic waves transmitted from the electromagnetic wave transmitting antenna 110 and diffusely reflected from the golf ball supporter 130 or the antenna supporters 115 and 125, thereby inhibiting the electromagnetic wave receiving antenna 120 from receiving noise. As shown therein, the absorber 162 may also be attached or applied to the antenna supporters 115 and 125.

The electromagnetic wave transmitting antenna 110 and the electromagnetic wave receiving antenna 120 may be connected to a detector 140. The detector 140 generates the electromagnetic waves, transmits and receives the electromagnetic waves through the electromagnetic wave transmitting antenna 110 and the electromagnetic wave receiving antenna 120, and outputs and detects the magnitude and phase of the received electromagnetic waves.

The detector 140 according to the disclosure may be configured in various forms. The detector 140 may include a transmitting circuit 1413 and a receiving circuit 1414, may include a network analyzer 1420, or may include a signal generator 1430 and a spectrum analyzer 1432, but is not limited thereto.

When the detector 140 includes the network analyzer 1420, the electromagnetic wave transmitting antenna 110 and the electromagnetic wave receiving antenna 120 are connected to the electromagnetic wave transmitting side and the electromagnetic wave receiving side of the network analyzer 1420, respectively. When the detector 140 includes the signal generator 1430 and the spectrum analyzer 1432, the electromagnetic wave transmitting antenna 110 is connected to the signal generator 1430 and the electromagnetic wave receiving antenna 120 is connected to the spectrum analyzer 1432.

The detector 140 may be connected to the analyzer 200 and transmit information about the magnitude and phase of the detected electromagnetic waves to the analyzer 200.

FIG. 3 shows an alternative example of the measurer 100 shown in FIG. 2. Below, descriptions will be made focusing on difference from the foregoing embodiments.

Referring to FIG. 3, according to this embodiment, the electromagnetic wave transceiving antenna 1120, into which the electromagnetic wave transmitting antenna 110 and the electromagnetic wave receiving antenna 120 are integrated, is provided.

The rotary supporter including the golf ball supporter 130 and the rotation unit 135 has the same configuration as described above.

An antenna supporter 1125 supports the electromagnetic wave transceiving antenna 1120. The antenna supporter 1125 is spaced apart from the golf ball supporter 130, and supports the electromagnetic wave transceiving antenna 1120 on the same horizontal surface as the measurement target golf ball supported by the golf ball supporter 130.

Like the embodiment shown in FIG. 2, the antenna supporter 1125 is slidably provided with respect to the golf ball supporter 130, and thus adjustable in distance from the golf ball supporter 130.

Unlike the embodiment shown in FIG. 2, the electromagnetic wave transceiving antenna 1120 may be connected to the detector 140 and receive only the reflected electromagnetic waves from the plurality of measurement sides of the measurement target golf ball.

The detector 140 is connected to the electromagnetic wave transceiving antenna 1120, transmits and receives the electromagnetic waves, detects the magnitude and phase of the received electromagnetic waves, and transmits a detection result to the analyzer 200.

Figure 4:
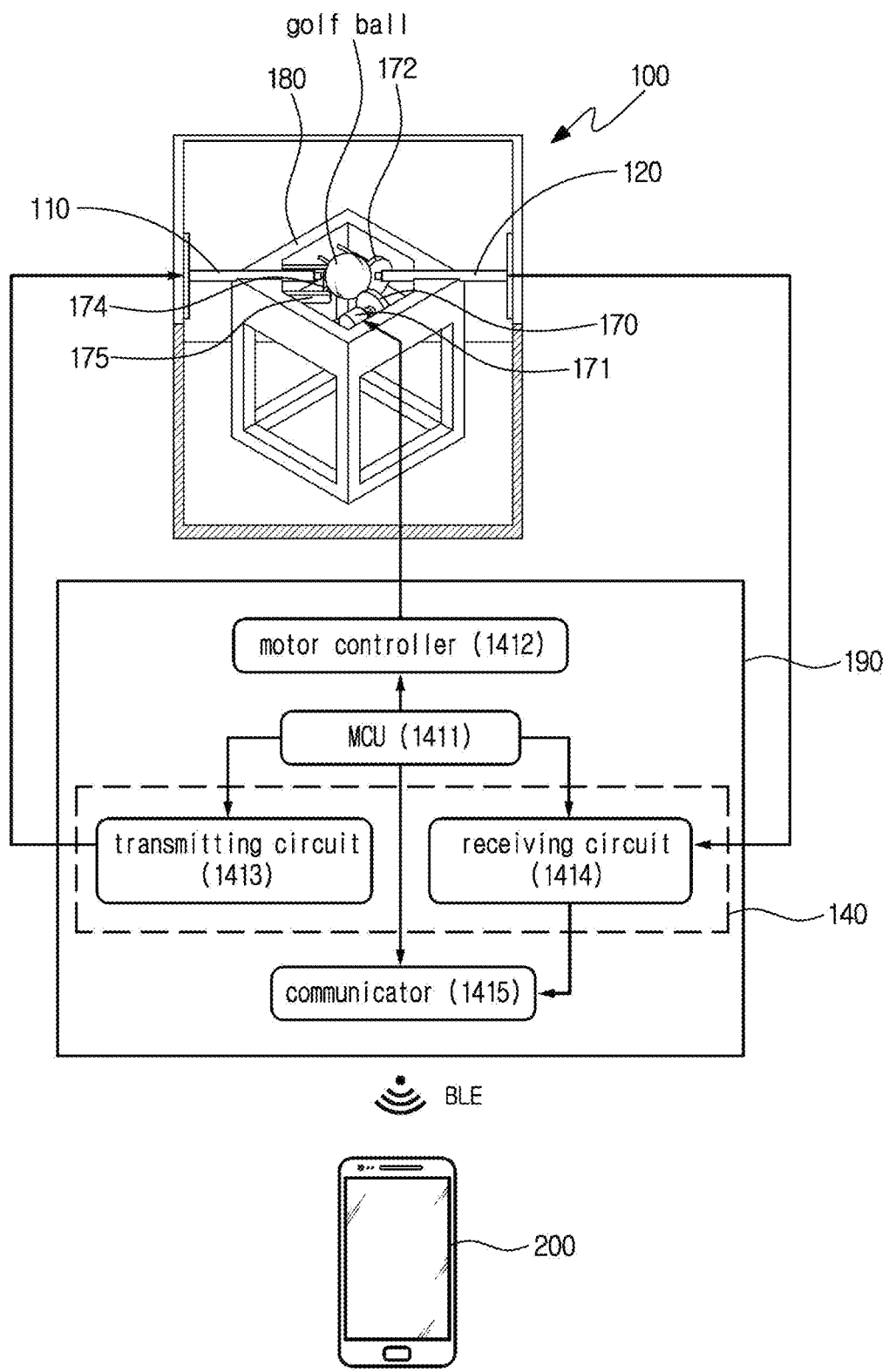
FIG. 4 is a view showing an apparatus for selecting a high-quality golf ball according to another embodiment of the disclosure.
Figure 5:
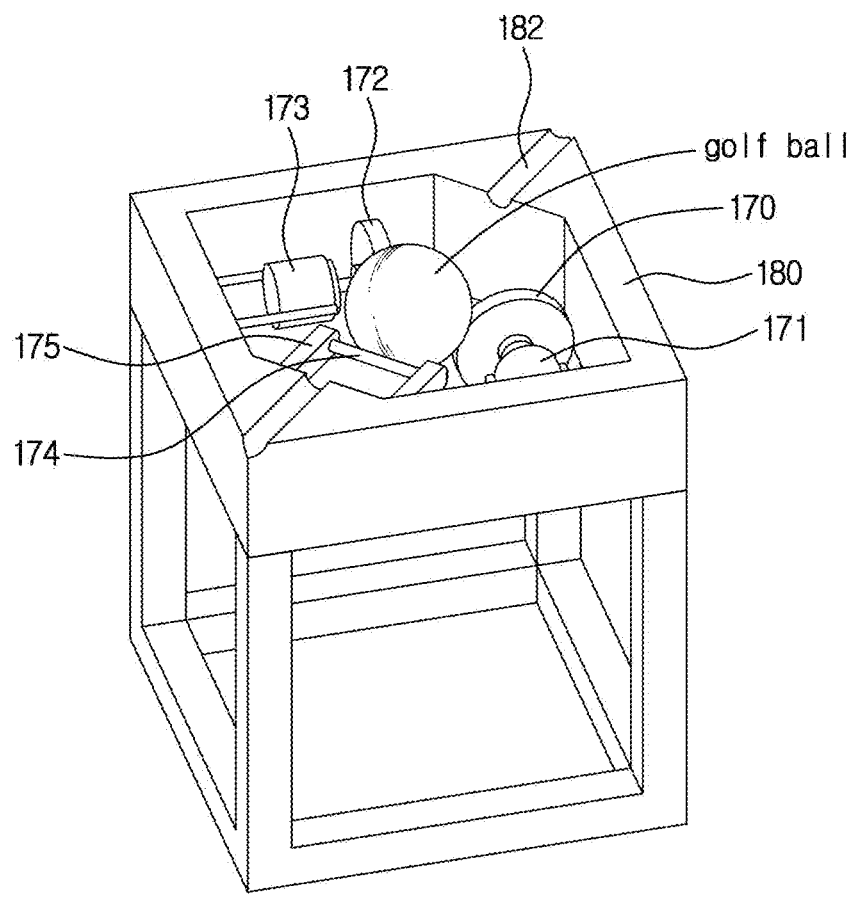
FIG. 5 is a perspective view showing details of a rotary supporter of FIG. 4.
Figure 6:
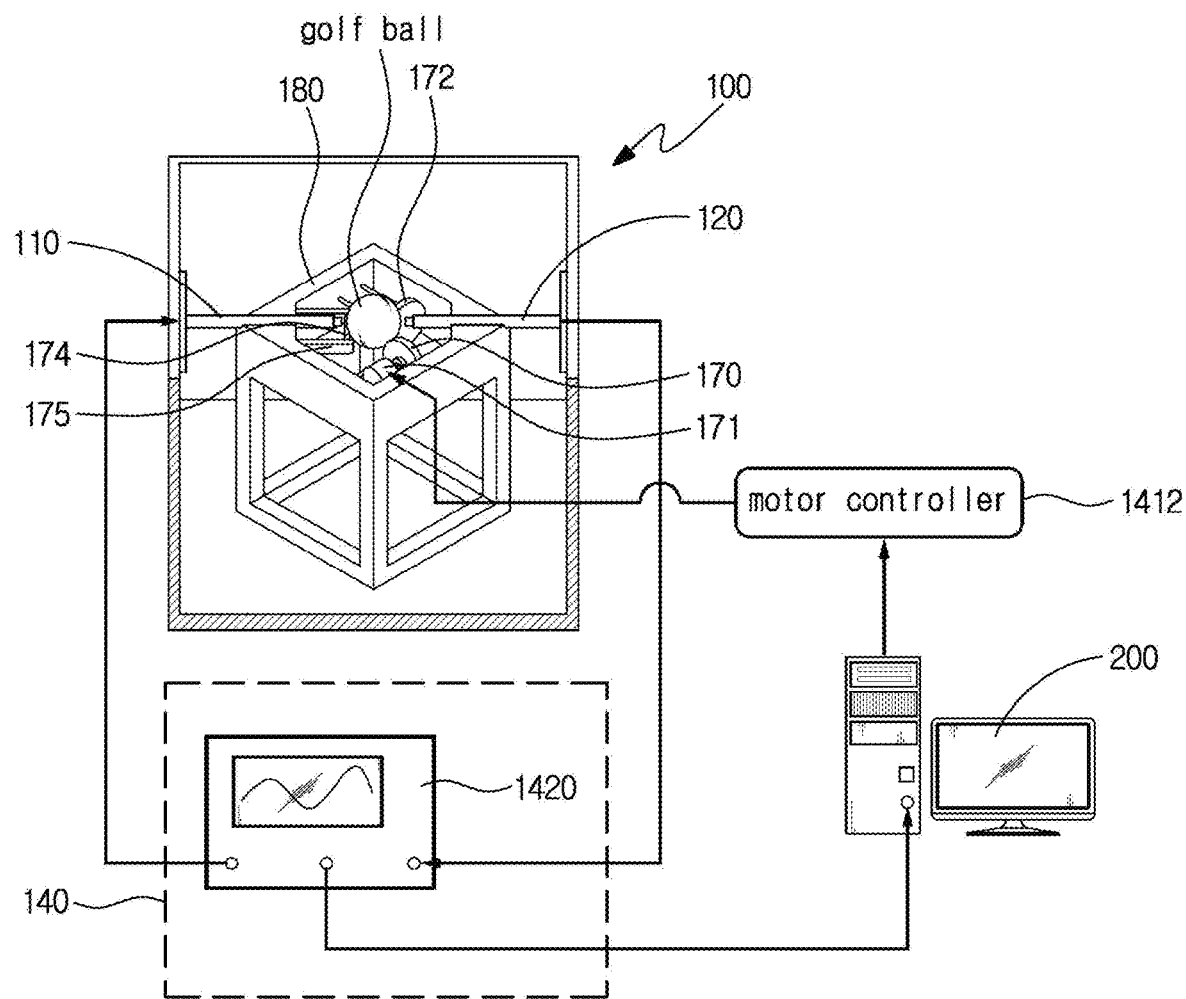
FIGS. 6 and 7 are views respectively showing alternative examples of a detector shown in FIG. 4.
Figure 7:
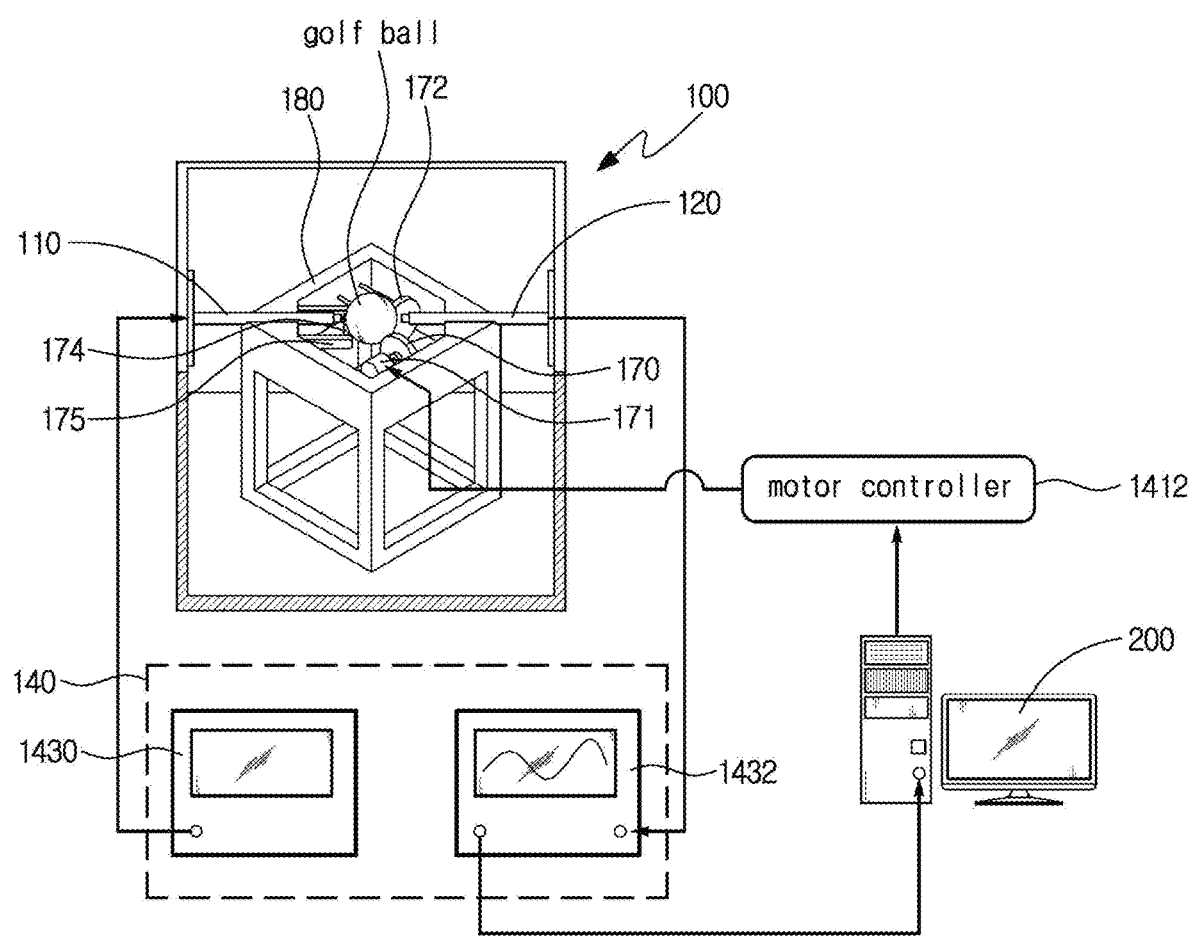
Figure 8:
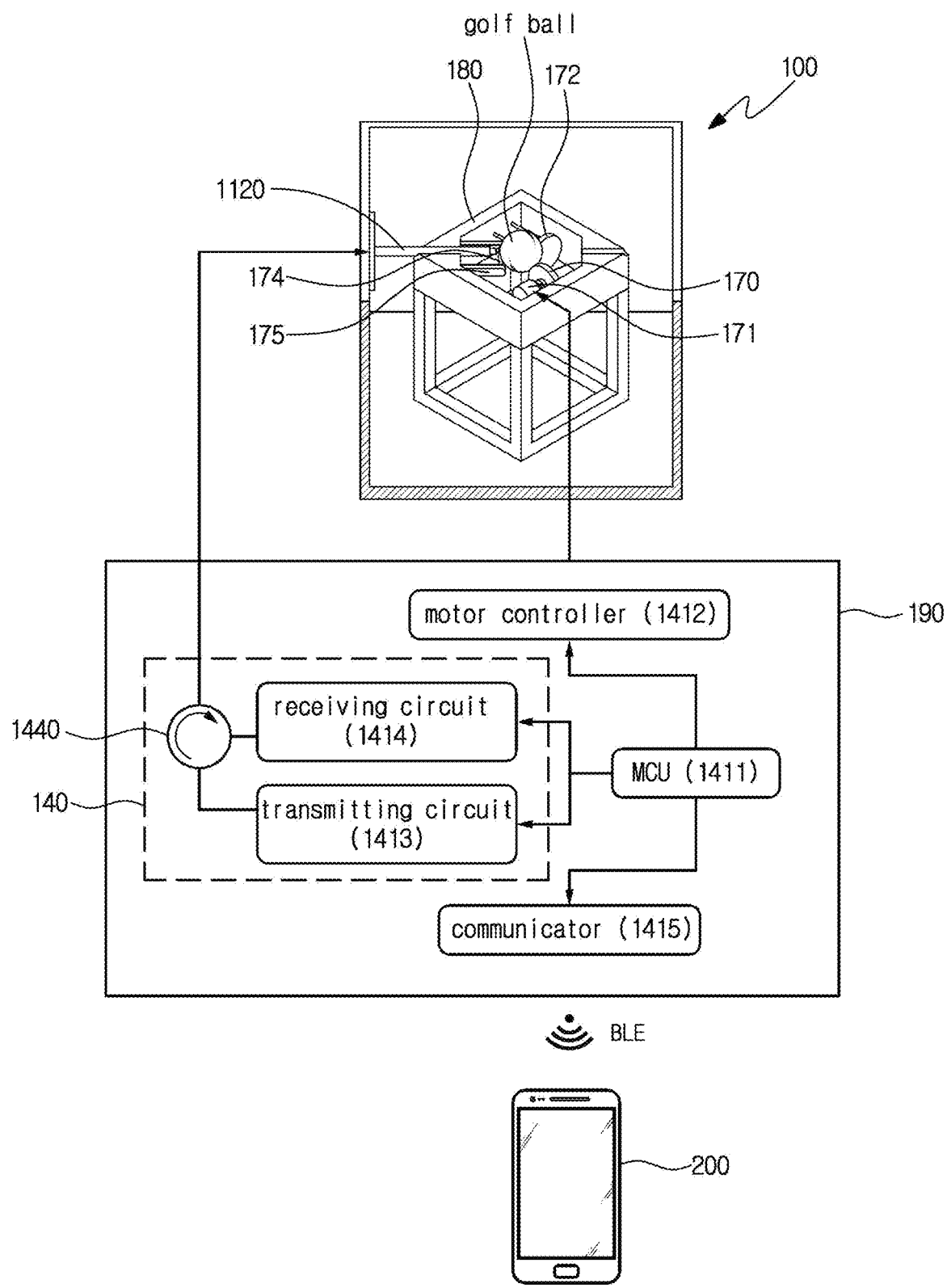
FIG. 8 shows an alternative example of FIG. 4.
Figure 9:
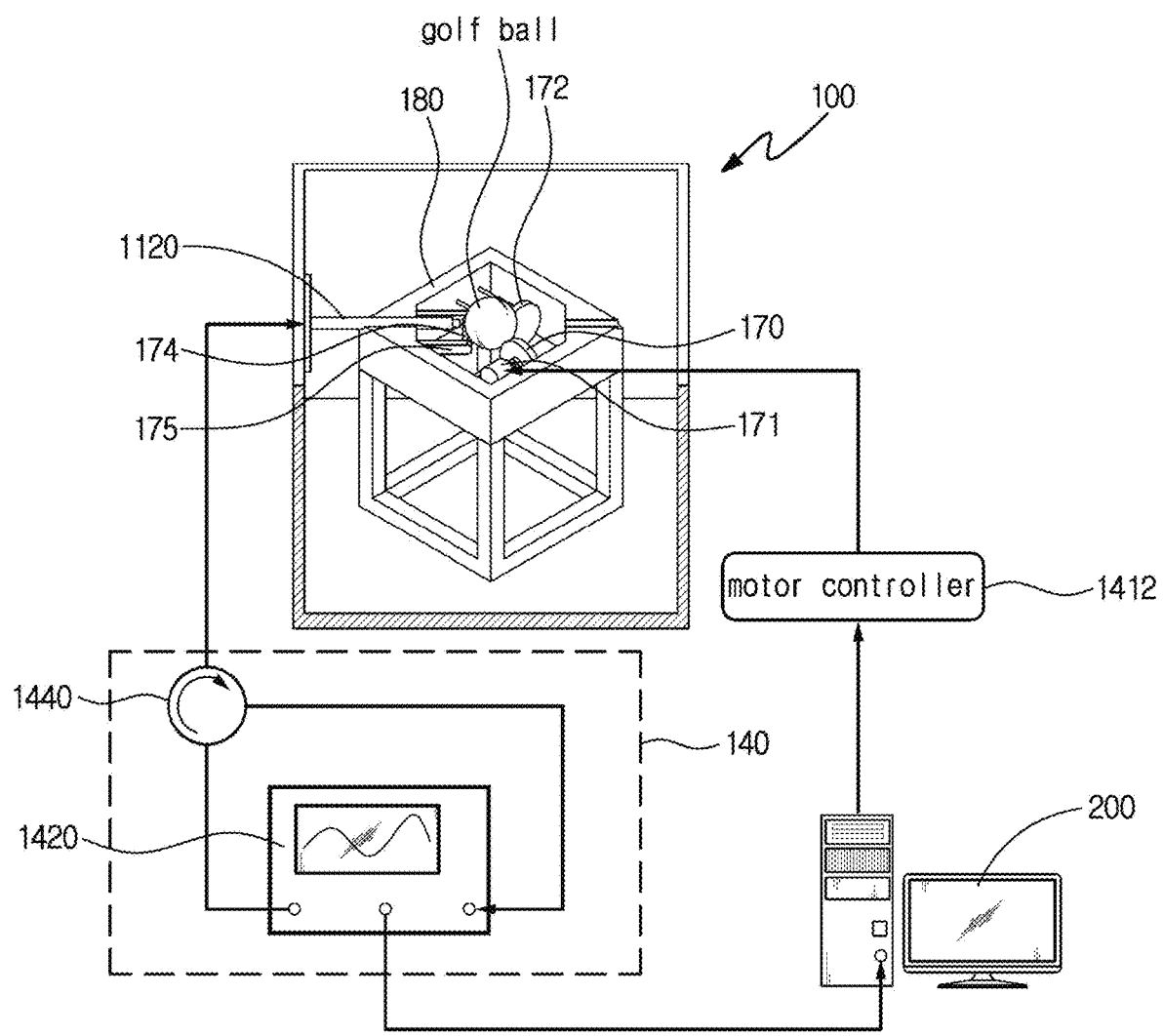
FIGS. 9 and 10 are views respectively showing alternative examples of a detector shown in FIG. 8.
Figure 10:
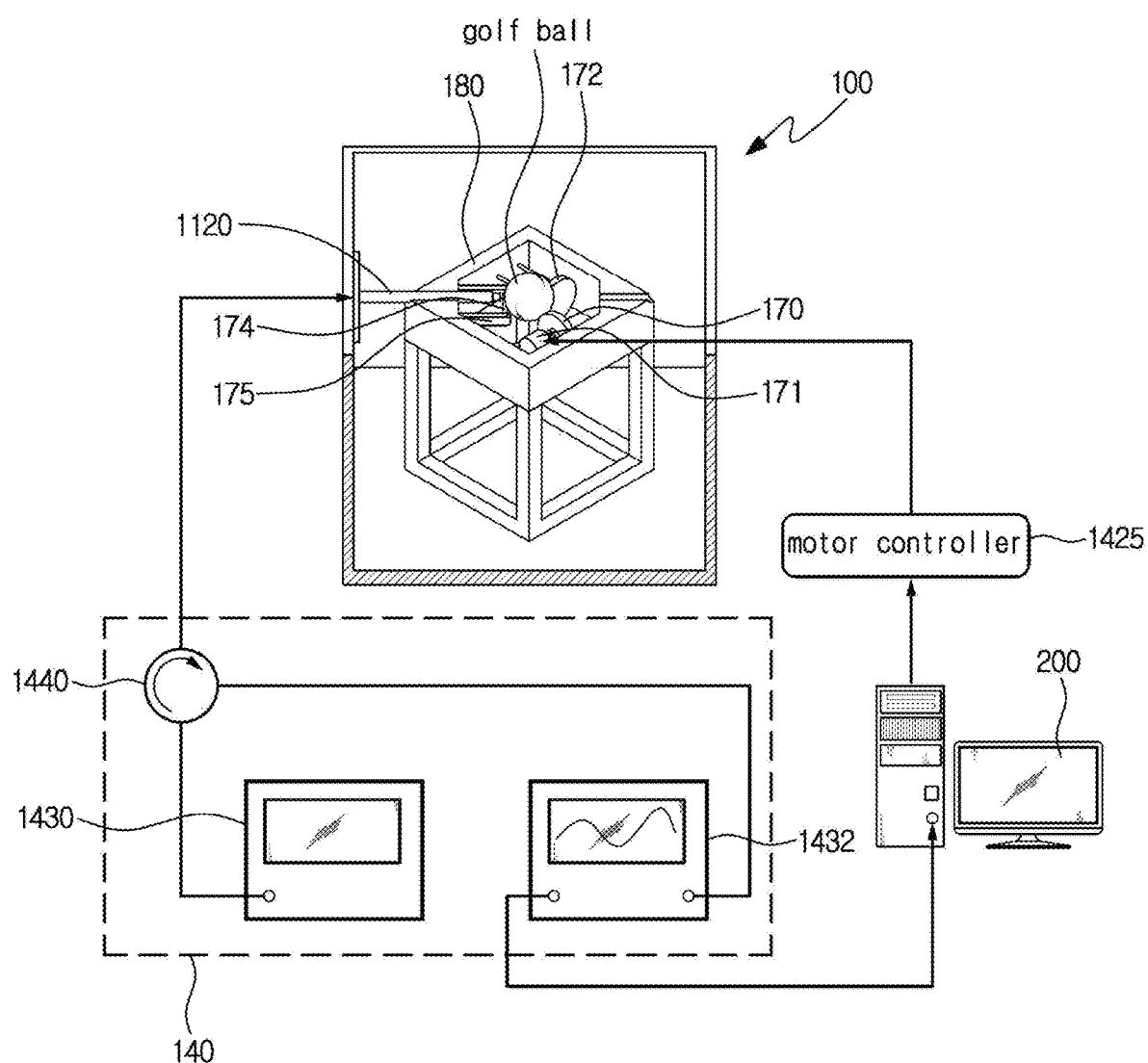

FIG. 4 is a view showing an apparatus for selecting a high-quality golf ball according to another embodiment of the disclosure, FIG. 5 is a perspective view showing details of a rotary supporter of FIG. 4, FIGS. 6 and 7 are views respectively showing alternative examples of a detector shown in FIG. 4, FIG. 8 shows an alternative example of FIG. 4, and FIGS. 9 and 10 are views respectively showing alternative examples of a detector shown in FIG. 8.

The measurer 100 according to this embodiment may include the rotary supporter, the electromagnetic wave transmitting antenna 110, and the electromagnetic wave receiving antenna 120.

The rotary supporter shown in FIG. 5 supports and rotates the golf ball, thereby changing the posture of the golf ball. The rotary supporter may include a first rotation supporting plate 170, a first motor 171 for rotating the first rotation supporting plate 170, a second rotation supporting plate 172, and a second motor 173 for rotating the second rotation supporting plate 172. In addition, the rotary supporter may further include a roll bar 174.

As shown therein, the first rotation supporting plate 170 and the first motor 171 may be supported by and fastened to a frame 180 having a hexahedral structure. The first rotation supporting plate 170 may be shaped like a disc or a cylinder, have an axis disposed in a horizontal direction parallel to the ground, and, as shown therein, use its lateral side to support a lateral side, i.e., a first point of the golf ball. A motor shaft of the first motor 171 is connected to the central axis of the first rotation supporting plate 170, so that the first rotation supporting plate 170 can rotate as the first motor 171 is driven. Therefore, the rotation of the first rotation supporting plate 170 makes the golf ball being supported at the first point be rotated, thereby changing the posture of the golf ball.

The second rotation supporting plate 172 and the second motor 173 may support a lateral side, i.e., a second point of the golf ball in the same manner as the first rotation supporting plate 170 and the first motor 171. In this case, the first rotation supporting plate 170 and the second rotation supporting plate 172 may be disposed to respectively support the golf ball in perpendicular direction from the center of the golf ball when we see from top to bottom, so the first point and the second point at which the golf ball is supported may be on the lines that pass through the center of the golf ball and are perpendicular to each other.

As the first rotation supporting plate 170 is rotated by the first motor 171 or the second rotation supporting plate 172 is rotated by the second motor 173, the golf ball may rotate in two directions perpendicular to each other. Therefore, the posture of the golf ball may be variously changed so that all the sides of the golf ball can face the stationarily disposed electromagnetic wave transmitting or receiving antenna 110 or 120.

The roll bar 174 refers to a bar which is freely rotatable at opposite sides thereof, and supports the third point of the golf ball at a middle outer surface thereof. In this case, as shown therein, the third point may be located in the middle of the opposite side to the first and second points with respect to the center of the golf ball when viewed downwards from above, and support the lower side of the golf ball when viewed from lateral sides. To support the roll bar 174, a pair of holding bars 175 may be extended inwards from the frame 180, so that the opposite ends of the roll bar 174 can be free-rotatably coupled to both ends of the holding bar 175.

Therefore, three points at the lower side of the golf ball are supported by the first rotation supporting plate 170, the second rotation supporting plate 172, and the roll bar 174, so that the roll bar 174 can freely rotate when the first rotation supporting plate 170 or the second rotation supporting plate 172 is driven to rotate by the motor, thereby stably supporting the golf ball.

The electromagnetic wave transmitting antenna 110 may be disposed at the first side of the golf ball and transmit a signal toward the golf ball. On the top surface of the frame 180, a seating groove 182 may be formed to easily fix the electromagnetic wave transmitting antenna 110.

The electromagnetic wave receiving antenna 120 may be disposed at the second side of the golf ball and receive the signal transmitted from the electromagnetic wave transmitting antenna 110 toward the golf ball and transmitted through the golf ball.

As shown in FIG. 4, a predetermined circuit board, i.e., a control board 190 may include a micro controller unit (MCU) 1411, a motor controller 1412 controlling the operation of the first motor 171 or the second motor 173, and the detector 140.

The detector 140 may include the transmitting circuit 1413 for generating a signal to be transmitted from the electromagnetic wave transmitting antenna 110 and transmitting the signal to the electromagnetic wave transmitting antenna 110, and the receiving circuit 1414 for receiving the signal received in the electromagnetic wave receiving antenna 120 and processing information about the magnitude and phase of the signal. A communicator 1415 may transmit the processed signal from the receiving circuit 1414 to an external device, i.e., the analyzer 200 including a smart phone, a smart pad, and the like terminal, a personal computer (PC), etc. The communicator 1415 may transmit data by a wire or wirelessly, and FIG. 4 shows a structure of using a Bluetooth low energy (BLE) signal to transmit the signal processed by the receiving circuit 1414 to the smart phone or the like terminal. The analyzer 200 receives and analyzes the signal to determine the uniformity of the golf ball and display a selection result on a screen of a display.

FIG. 6 shows an alternative example of the detector 140 in FIG. 4. In this embodiment, the network analyzer 1420 that generates a signal to be transmitted from the electromagnetic wave transmitting antenna 110, transmits the signal to the electromagnetic wave transmitting antenna 110, and processes the signal received in the electromagnetic wave receiving antenna 120 is used as the foregoing transceiving circuit. In this case, the information about the magnitude and phase of the processed signal may be transmitted from the network analyzer 1420 to the analyzer 200 in real time. In this embodiment, the PC is illustrated as the analyzer 200. The operation of the motor controller 1412 for driving the first motor 171 or the second motor 173 may be controlled by a control command of the PC.

FIG. 7 shows another alternative example of the detector in FIG. 4. In this embodiment, the signal generator 1430 that generates a signal to be transmitted from the electromagnetic wave transmitting antenna 110 and transmits the signal to the electromagnetic wave transmitting antenna 110, and the spectrum analyzer 1432 that receives and processes the signal received in the electromagnetic wave receiving antenna 120 are used as the transceiving circuit. In this case, the information about the magnitude and phase of the signal processed by the spectrum analyzer 1432 may be transmitted to the analyzer 200 in real time. Even in this embodiment, the PC is illustrated as the analyzer 200.

Even in this embodiment, the operation of the motor controller 1412 for driving the first motor 171 or the second motor 173 may be controlled by a control command of the PC.

FIG. 8 shows an alternative example of the measurer 100 shown in FIG. 4. Below, descriptions will be made focusing on difference from the foregoing embodiments.

Referring to FIG. 8, according to this embodiment, the electromagnetic wave transceiving antenna 1120, into which the electromagnetic wave transmitting antenna 110 and the electromagnetic wave receiving antenna 120 are integrated, is provided.

The apparatus for selecting a high-quality golf ball according to this embodiment may include the rotary supporter, the electromagnetic wave transceiving antenna 1120, and the analyzer 200.

In the foregoing embodiment described above with reference to FIG. 4, the electromagnetic wave transmitting antenna 110 disposed at the first side of the golf ball and the electromagnetic wave receiving antenna 120 disposed at the second side of the golf ball are used in such a manner that the signal transmitted from the electromagnetic wave transmitting antenna 110 and transmitted through the golf ball is received in the electromagnetic wave receiving antenna 120, thereby selecting a high-quality golf ball based on the received signal. On the other hand, the electromagnetic wave transceiving antenna 1120 according to this embodiment is placed at the first side of the golf ball, transmits the signal toward the golf ball, and receives a signal reflected from the golf ball.

As shown in FIG. 8, like the foregoing embodiment of FIG. 4, the control board 190 according to this embodiment may include a MCU 1411, the motor controller 1412 for controlling the operation of the motor, the transmitting circuit 1413 for generating a signal to be transmitted from the electromagnetic wave transceiving antenna 1120 and transmitting the signal the electromagnetic wave transceiving antenna 1120, the receiving circuit 1414 for processing the signal received from the electromagnetic wave transceiving antenna 1120, and the communicator 1415 for transmitting the processed signal from the receiving circuit 1414 to the analyzer 200 provided as the external terminal or the PC.

In addition, as shown in FIG. 9, like the embodiment shown in FIG. 6, the network analyzer 1420 that generates a signal to be transmitted from the electromagnetic wave transceiving antenna 1120, transmits the signal to the electromagnetic wave transceiving antenna 1120, and processes the signal received in the electromagnetic wave transceiving antenna 1120 may be used as the foregoing transceiving circuit. In this case, the information about the magnitude and phase of the processed signal may be transmitted from the network analyzer 1420 to the analyzer 200 in real time, so that a selection result can be displayed on a monitor.

Here, the operation of the motor controller 1412 for driving the first motor 171 or the second motor 173 may be controlled by a control command of the PC.

In addition, as shown in FIG. 10, like the embodiment shown in FIG. 7, the signal generator 1430 that generates a signal to be transmitted from the electromagnetic wave transceiving antenna 1120 and transmits the signal to the electromagnetic wave transceiving antenna 1120, and the spectrum analyzer 1432 that receives and processes the signal received in the electromagnetic wave transceiving antenna 1120 may be used as the transceiving circuit. In this case, the information about the magnitude and phase of the signal processed by the spectrum analyzer 1432 may be transmitted to the analyzer 200 in real time, so that a selection result of the analyzer 200 can be displayed on the monitor.

Even in this embodiment, the operation of the motor controller 1412 for driving the first motor 171 or the second motor 173 may be controlled by a control command of the PC.

However, in the embodiments shown in FIGS. 8 to 10, the detector 140 may additionally include a circulator 1440 for distinguishing between a transmitted signal and a received signal while the signal is being transmitted and received.

Below, the principle of selecting a high-quality golf ball and the experimental results from selection effects will be described according to the disclosure.

Figure 11:
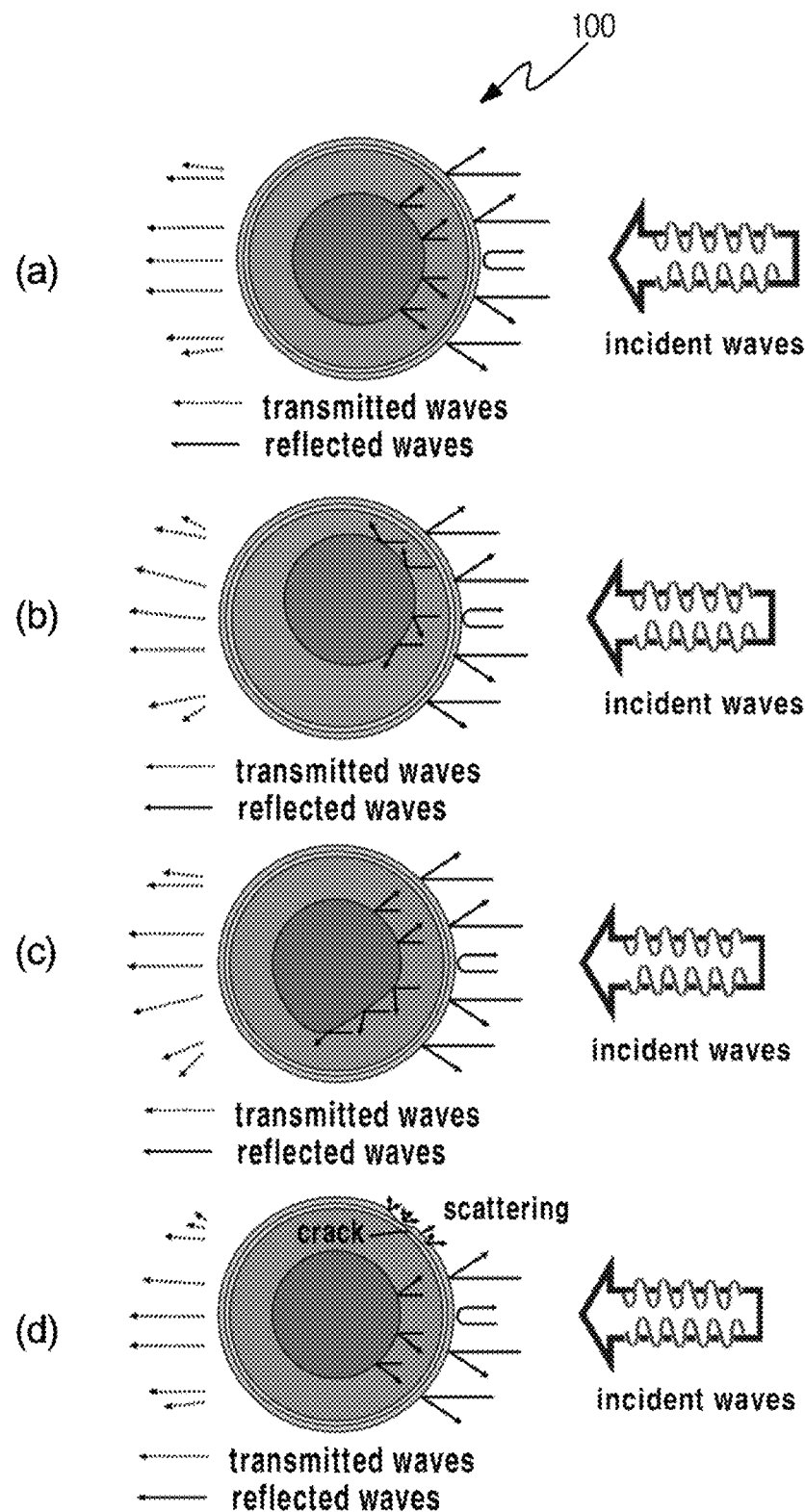
FIG. 11 is a view illustrating electromagnetic signals transmitted through and reflected from (a) a golf ball with internal and external symmetry, (b) a golf ball with an eccentric core, (c) a golf ball with an asymmetric and imbalanced core, and (d) a golf ball with a damaged cover.
Figure 12:
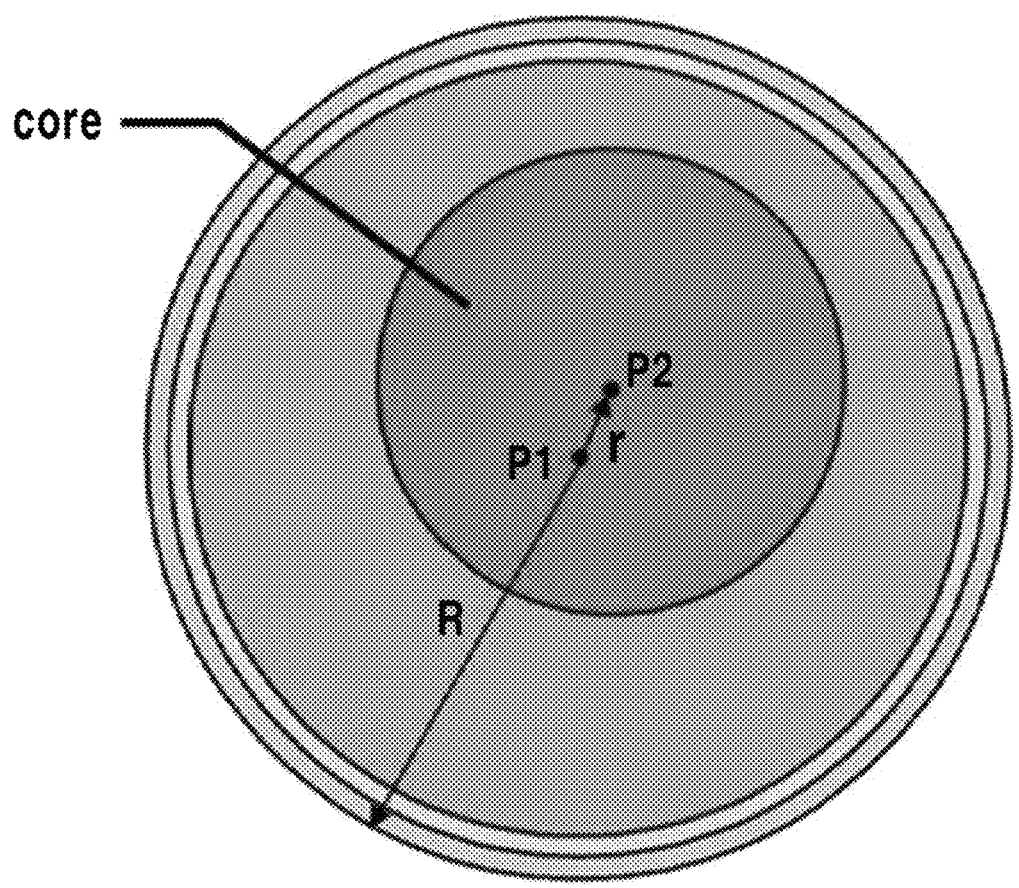
FIG. 12 is a cross-sectional view for explaining the eccentricity of a golf ball.

FIG. 11 is a view illustrating electromagnetic signals transmitted through and reflected from (a) a golf ball with internal and external symmetry, (b) a golf ball with an eccentric core, (c) a golf ball with an asymmetric and imbalanced core, and (d) a golf ball with a damaged cover, and FIG. 12 is a cross-sectional view for explaining the eccentricity of a golf ball.

The golf ball may include a core, an inner shell, and an outer shell which are different in material from one another. For example, the golf ball may include a core made of rubber, an inner shell layer made of plastic, and an outer shall layer made of thermosetting polyurethane, thermoplastic polyurethane, or ionomer plastic. Besides, various materials have been developed and applied to the golf ball in order to increase the driving distance of the golf ball, and complex materials for each manufacturer may be mixed into the golf ball.

When the electromagnetic waves transmitted from the electromagnetic wave transmitting antenna 110 or the electromagnetic wave transceiving antenna 1120 are incident to the golf ball, the incident waves are scattered and transmitted on the interface between different materials that constitute the golf ball. In this case, the reflected waves may be returned to the electromagnetic wave transceiving antenna 1120, and the transmitted waves may be received in the electromagnetic wave receiving antenna 120 on the opposite side. The reflection and transmission characteristics of the electromagnetic waves are very sensitive to the dielectric constant of the medium in the golf ball, and therefore the magnitude and phase characteristics of the reflected or transmitted electromagnetic waves may be varied depending on the uniformity of the medium inside the golf ball.

As shown in (a) of FIG. 11, when the inside of the golf ball is symmetrically and uniformly manufactured with respect to the structural/physical properties, the reflection or transmission characteristics measured while rotating the golf ball may be uniform. In this case, the core and outer shell of the golf ball are different in physical properties from each other, and the diameter of the golf ball is approximately 42 mm. With such physical properties of the core and outer shell in the golf ball, the measurement may be performed by selecting a frequency at which reactivity is high.

On the other hand, when the core layer is eccentrically arranged toward a certain direction inside the golf ball as shown in (b) of FIG. 11 or when the medium of the core layer is asymmetric inside the golf ball as shown in (c) of FIG. 11, the electromagnetic waves reflected or transmitted for each measurement side are different in characteristics.

In addition, even when the outer cover of the golf ball is asymmetrically damaged as shown in (d) of FIG. 11, the electromagnetic waves reflected or transmitted for each measurement side may be different in characteristics. Because the external damage is relatively very small compared to the size of the golf ball, the measurement may be performed at a frequency higher than that of when the balance and eccentricity in the golf ball are detected.

Therefore, according to the disclosure, the internal uniformity of the golf ball may be quantified and evaluated based on the characteristics of the electromagnetic waves measured while the golf ball is rotated by the rotary supporter (e.g., based on the uniformity of the magnitude and phase of the reflected or transmitted signal).

Referring to FIG. 12, the eccentricity may be expressed with a distance r from the center P1 of the golf ball to the center P2 of the core with respect to the radius R of the golf ball as shown in the Equation 1.

$$\text{Eccentricity}(\varepsilon) = r(\text{the distance from the center of the golf ball to the center of the core})/R(\text{the radius of the golf ball}) \quad [\text{Equation 1}]$$

As can be seen from the Equation 1, when the core is exactly at the center of the golf ball and the center of the golf ball matches the center of and the core, the distance r from the center of the golf ball to the center of the core becomes 0, and therefore the eccentricity also becomes 0. On the other hand, r increases and the eccentricity also increases as the distance from the center of the golf ball to the center of the core increases.

Figure 13:
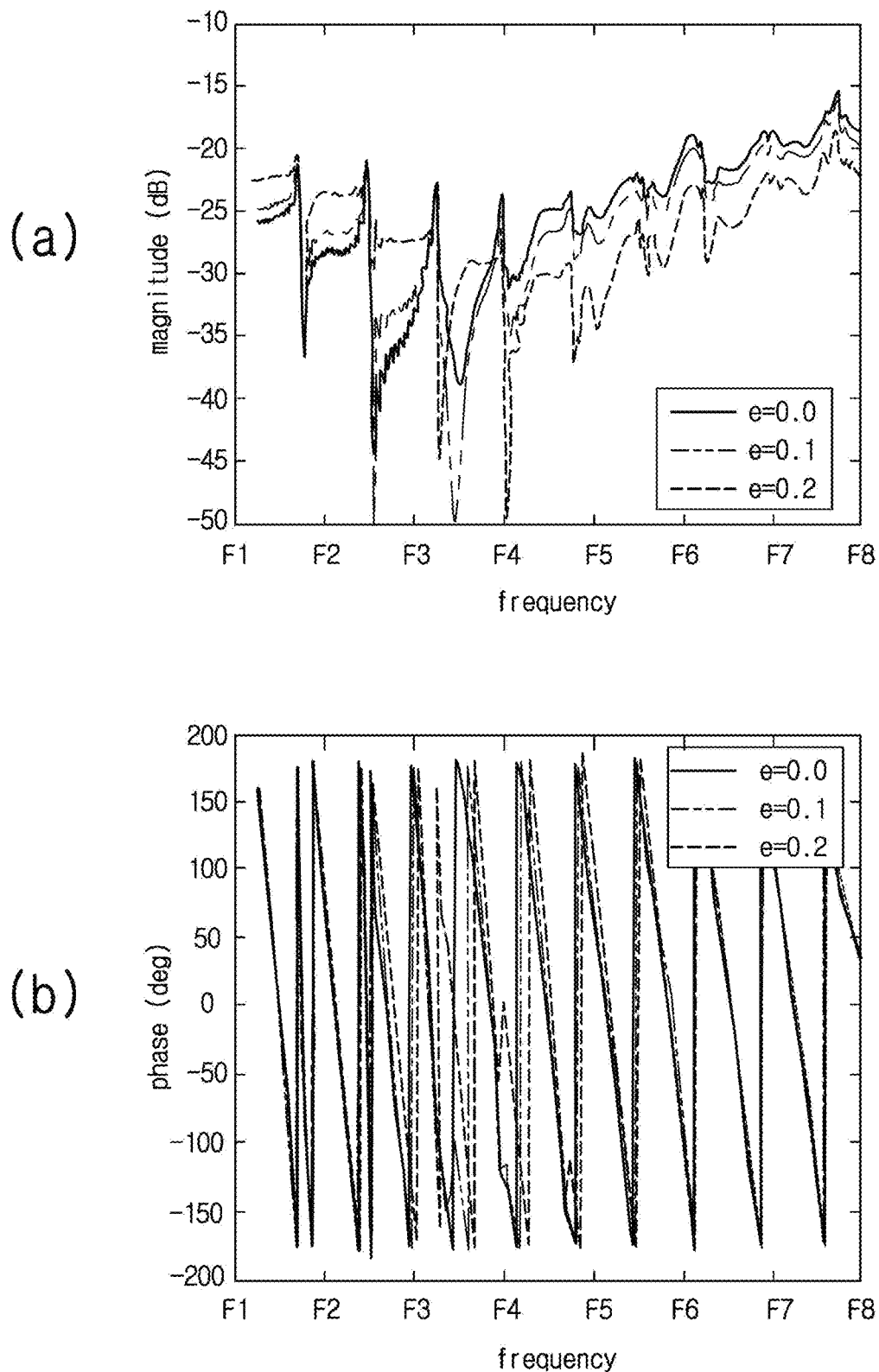
FIGS. 13 and 14 are graphs showing the results of measuring electromagnetic wave transmission characteristics by an apparatus for selecting a high-quality golf ball according to the disclosure.
Figure 14:
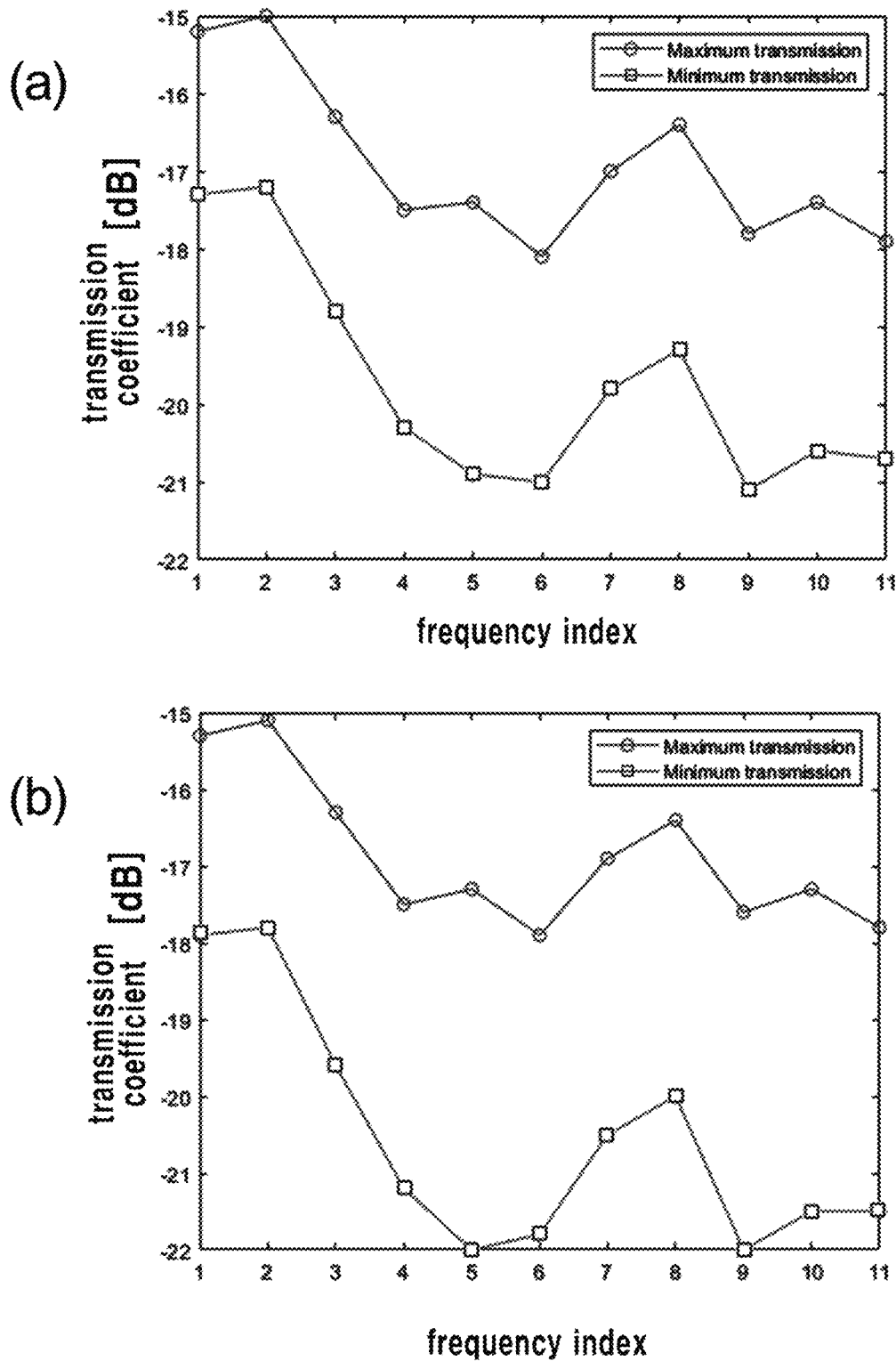
Figure 15:
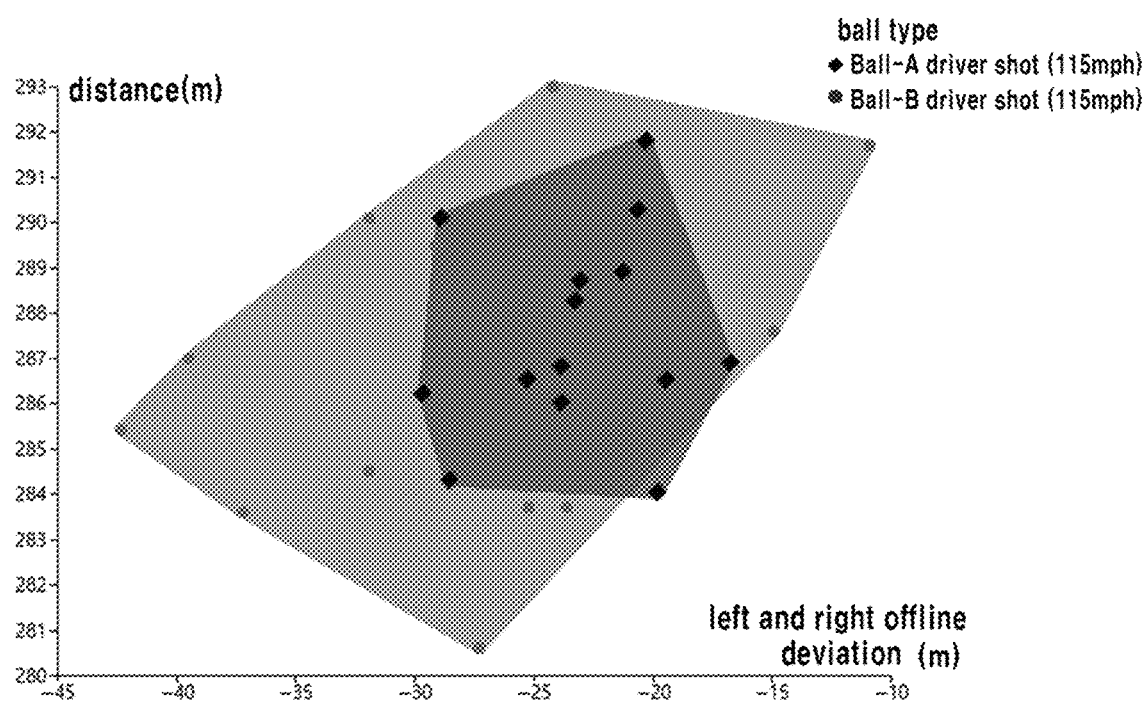
FIG. 15 is a graph showing the results of driver shots at a switching speed of 115 mph with respect to a ball selected in (a) of FIG. 14 and a ball selected in (b) of FIG. 14.
Figure 16:
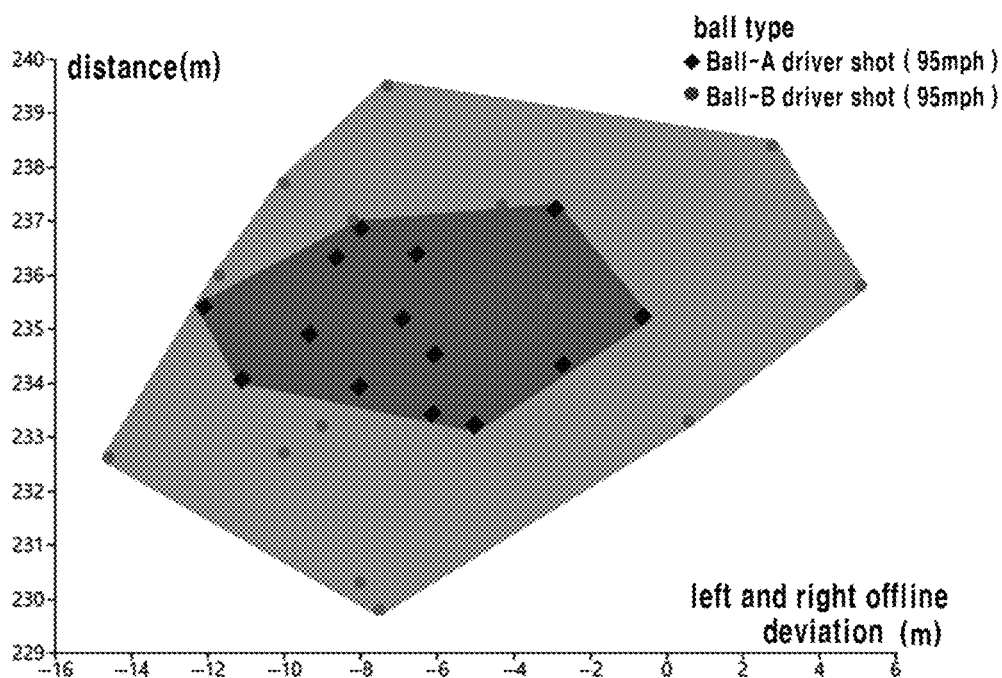
FIG. 16 is a graph showing the results of driver shots at a switching speed of 95 mph with respect to a ball selected in (a) of FIG. 14 and a ball selected in (b) of FIG. 14.
Figure 17:
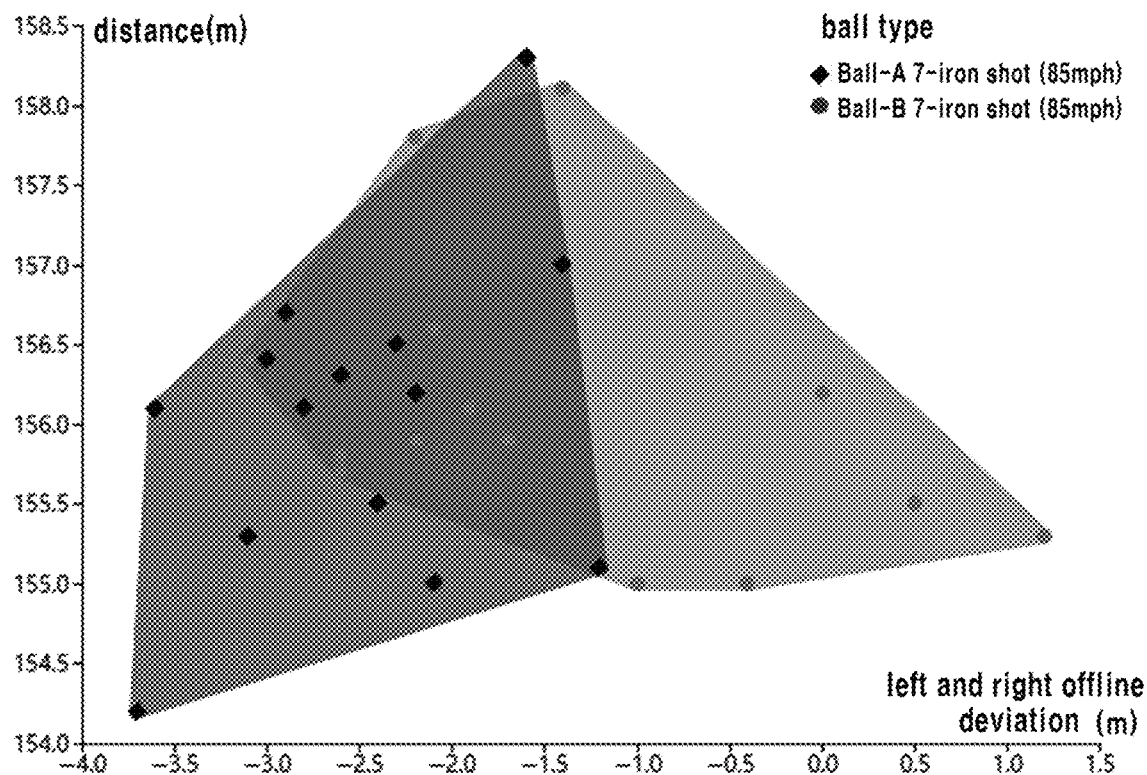
FIG. 17 is a graph showing the results of 7-iron shots at a switching speed of 85 mph with respect to a ball selected in (a) of FIG. 14 and a ball selected in (b) of FIG. 14.
Figure 18:
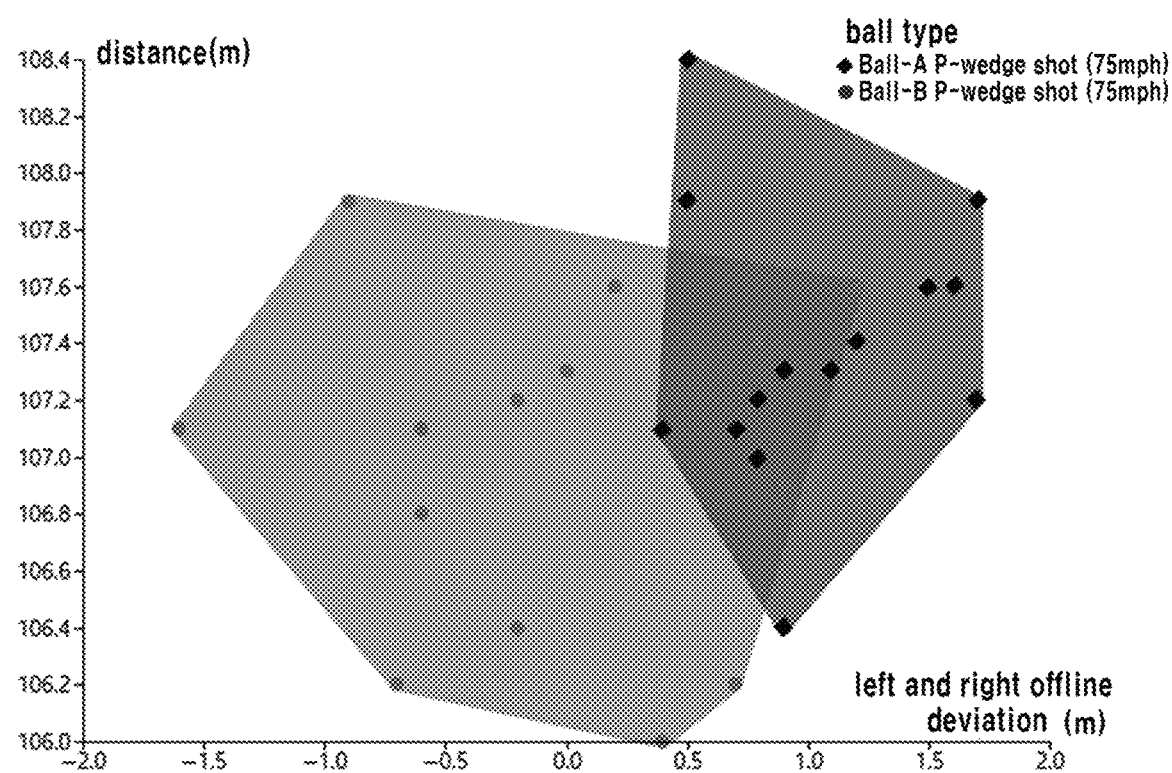
FIG. 18 is a graph showing the results of pitching wedge shots at a switching speed of 115 mph with respect to a ball selected in (a) of FIG. 14 and a ball selected in (b) of FIG. 14.

FIGS. 13 and 14 are graphs showing the results of measuring electromagnetic wave transmission characteristics by an apparatus for selecting a high-quality golf ball according to the disclosure, FIG. 15 is a graph showing the results of driver shots at a switching speed of 115 mph with respect to a ball selected in (a) of FIG. 14 and a ball selected in (b) of FIG. 14, FIG. 16 is a graph showing the results of driver shots at a switching speed of 95 mph with respect to a ball selected in (a) of FIG. 14 and a ball selected in (b) of FIG. 14, FIG. 17 is a graph showing the results of 7-iron shots at a switching speed of 85 mph with respect to a ball selected in (a) of FIG. 14 and a ball selected in (b) of FIG. 14, and FIG. 18 is a graph showing the results of pitching wedge shots at a switching speed of 115 mph with respect to a ball selected in (a) of FIG. 14 and a ball selected in (b) of FIG. 14.

In FIG. 13, (a) shows the magnitude at the frequency of the electromagnetic waves received according to the eccentricity of a defective golf ball, and (b) shows the phase at the frequency of the electromagnetic waves received according to the eccentricity of the defective golf ball. Referring to FIG. 13, both the magnitude and phase of the transmitted electromagnetic waves were varied depending on change in eccentricity. As the eccentricity increased from 0 to 0.2, the transmission gradually increased at a frequency lower than the frequency F3, but gradually decreased at a frequency higher than the frequency F3.

In particular, the magnitude and phase of electromagnetic waves were sensitively varied between certain frequencies F2 and F5 depending on the degree of eccentricity. Therefore, the degree of imbalanced symmetricity such as the eccentricity inside the golf ball may be estimated based on the transmission and reflection characteristics of the electromagnetic waves.

In particular, the eccentricity and the balance may be quantified by applying a set of data about the eccentricity and the transmission and reflection characteristics to a deep learning technique, and it is thus possible to automatically select a defective golf ball.

FIG. 14 shows results of measuring the electromagnetic wave transmission characteristics of specific brand golf ball available on the market an apparatus for selecting a high-quality golf ball according to the disclosure. A golf ball (Ball-A) having the lowest sum of deviation (SOD) between the maximum transmission coefficient and the minimum transmission coefficient measured while rotating golf balls in the same package box (see (a) in FIG. 4), and a golf ball (Ball-B) having the highest SOD (see (b) in FIG. 14) were selected.

According to the measurement results of FIG. 14, the maximum transmission coefficients of the golf balls Ball-A and Ball-B were almost the same, but the minimum transmission coefficients of the golf ball Ball-B was lower than that of the golf ball Ball-A by about 1 dB at all measurement frequencies.

To verify how different the flight characteristics (driving distance and left and right deviation) between the selected golf balls Ball-A and Ball-B are when the golf ball is actually hit with a golf club, a swing robot of Korea institute of golf and sports (KIGOS) was used in a test. Because the swing robot can repeat swing motions with the same speed and mechanism unlike a human, the same spot on a club face may be hit every swing. The flight trajectory of the golf ball was analyzed using the Foresight's GC Quad launch monitor. The GC Quad launch monitor can provide precise flight trajectory results only based on the characteristics of the golf ball because external factors affecting the flight of the golf ball, such as wind and humidity are excluded.

Driver shots were tested at two swing speeds of 95 mph and 115 mph (medium speed and fast speed). The Titleist's TSi2 drivers with a regular flex shaft of 65 g and an X-flex shaft with 75 g were used for 95 and 115 mph swings, respectively. Further, the same tests were repeated for a 7-iron (85 mph) and a pitching wedge (75 mph) of the Fourteen's TC-544 forged iron.

Further, numbers from '1' to '14' were marked on the surface of each golf ball to make 14 different points of each golf ball be hit by the test clubs, and thus the driving distance and left and right offline deviation between 14 driver shots were measured for each golf ball.

According to the results of driver shot tests at the swing speeds of 115 mph and 95 mph, the difference between the golf balls Ball-A and Ball-B was clear (see FIGS. 15 and 16). The golf ball Ball-A with a lower SOD showed that the driving distances had a smaller deviation. Above all, it should be noted that the left and right offline deviation of the golf ball Ball-A was much lower than that of the golf ball Ball-B. The golf ball Ball-B with a higher SOD showed that its offline deviation was 2.4 times higher than that of the golf ball Ball-A. The test results of the 7-iron and pitching wedge shots are also shown in FIGS. 17 and 18, and it will be understood that the golf ball Ball-A with a lower SOD showed better consistency than that of the golf ball Ball-B with a higher SOD.

The disclosure is not limited to the foregoing embodiments but may be implemented in various embodiments within the scope of the appended claims. Even various extends, to which various changes can be made by anyone who has ordinary knowledge in the art to which the disclosure pertains, fall within the scope of the appended claims without departing from the scope of the disclosure based on the appended claims.

The invention claimed is:

1. An apparatus for selecting a high-quality golf ball, comprising:
   a measurer configured to transmit a signal toward a golf ball and receive a signal transmitted through the golf ball; and
   an analyzer configured to select a golf ball by analyzing the received signal,
   wherein the measurer comprises:
      a rotary supporter configured to rotatably support the golf ball;
      an electromagnetic wave transmitting antenna disposed at a first side of the golf ball and configured to transmit electromagnetic waves toward the golf ball; and
      an electromagnetic wave receiving antenna disposed at a second side of the golf ball and configured to receive electromagnetic waves transmitted from the electromagnetic wave transmitting antenna.

2. The apparatus of claim 1, wherein;
   the rotary supporter comprises a golf ball supporter to support the golf ball to be vertically spaced apart from the ground; and a rotation unit to rotate the golf ball supporter with respect to a vertical axis, and
   the apparatus further comprises a first antenna supporter and a second antenna supporter that are spaced apart from the golf ball supporter and respectively support the electromagnetic wave transmitting antenna and the electromagnetic wave receiving antenna to be located on a same horizontal plane as the golf ball supported by the golf ball supporter.

3. The apparatus of claim 2, further comprising a base configured to support the golf ball supporter and the antenna supporter on one side thereof,
   wherein the base comprises an absorber attached or applied to the one side of the base and configured to absorb diffusely reflected electromagnetic waves.

4. The apparatus of claim 2, wherein the antenna supporter is slidably provided with respect to the golf ball supporter and adjustable in distance from the golf ball supporter.

5. The apparatus of claim 2, wherein
   the rotary supporter comprises:
   a first rotation supporting plate configured to support a first point on a lateral side of the golf ball and be rotated by a motor; and
   a second rotation supporting plate configured to support a second point on a lateral side of the golf ball and be rotated by a motor.

6. The apparatus of claim 5, wherein the first point and the second point are two points orthogonal to each other with respect to a center of the golf ball when viewed from top to bottom.

7. The apparatus of claim 5, wherein the rotary supporter further comprises a roll bar that is freely rotatable at opposite sides thereof, and supports a third point of the golf ball.

8. The apparatus of claim 1, wherein
   the signal comprises electromagnetic waves, and
   the apparatus further comprises a detector configured to generate and transceive the electromagnetic waves, and output and detect a magnitude and phase of the received electromagnetic waves.

9. The apparatus of claim 8, wherein the detector comprises a transmitting circuit and a receiving circuit, comprises a network analyzer, or comprises a signal generator and a spectrum analyzer.

10. The apparatus of claim 1, wherein the analyzer is configured to select a high-quality golf ball, which is internally and externally uniform and close to symmetry, based on uniformity of a signal received with respect to a plurality of measurement sides while rotating the golf ball.

11. The apparatus of claim 10, wherein the analyzer is configured to select a high-quality golf ball, which is internally and externally uniform and close to symmetry, based on uniformity of the magnitude and phase of the signal received with respect to the plurality of measurement sides.

12. The apparatus of claim 1, wherein the analyzer is configured to select a high-quality golf ball, which is internally and externally uniform and close to symmetry, based on a magnitude and phase of the signal received with respect to the plurality of measurement sides based on deep learning.

13. An apparatus for selecting a high-quality golf ball, comprising:
   a measurer configured to transmit a signal toward a golf ball and receive a signal reflected from the golf ball; and
   an analyzer configured to select a golf ball by analyzing the received signal,
   wherein the measurer comprises:
      a rotary supporter configured to rotatably support the golf ball; and
      an electromagnetic wave transceiving antenna disposed at a first side of the golf ball and configured to transmit electromagnetic waves toward the golf ball and receive reflected electromagnetic waves from the golf ball.

14. The apparatus of claim 13, wherein;
   the rotary supporter comprises a golf ball supporter to support the golf ball to be vertically spaced apart from the ground; and a rotation unit to rotate the golf ball supporter with respect to a vertical axis, and
   the apparatus further comprises an antenna supporter that is spaced apart from the golf ball supporter and supports the electromagnetic wave transceiving antenna to be located on a same horizontal plane as the golf ball supported by the golf ball supporter.

* * * * *